(12) United States Patent
Wang

(10) Patent No.: US 7,779,670 B2
(45) Date of Patent: Aug. 24, 2010

(54) TWO VALVE SWITCHING MODULATOR FOR COMPREHENSIVE TWO-DIMENSIONAL GAS CHROMATOGRAPHY

(75) Inventor: Frank C Wang, Annandale, NJ (US)

(73) Assignee: ExxonMobil Reseach and Engineering Company, Annandale, NJ (US)

( * ) Notice: Subject to any disclaimer, the term of this patent is extended or adjusted under 35 U.S.C. 154(b) by 394 days.

(21) Appl. No.: 11/716,325

(22) Filed: Mar. 9, 2007

(65) Prior Publication Data
US 2007/0214866 A1    Sep. 20, 2007

Related U.S. Application Data

(60) Provisional application No. 60/781,996, filed on Mar. 14, 2006.

(51) Int. Cl.
*G01N 30/04* (2006.01)
(52) U.S. Cl. ............................. 73/23.42; 96/105; 96/106
(58) Field of Classification Search ................ 73/23.42; 96/105, 106
See application file for complete search history.

(56) References Cited

U.S. PATENT DOCUMENTS

| 3,150,517 | A  | * | 9/1964 | Kuffer et al. | ................ | 73/23.42 |
| 5,196,039 | A  | * | 3/1993 | Phillips et al. | .............. | 210/656 |
| 6,354,671 | B1 | * | 3/2002 | Feldmann et al. | ............. | 303/15 |
| 7,383,718 | B2 | * | 6/2008 | McCurry et al. | ............. | 73/23.4 |

OTHER PUBLICATIONS

Mohler, R. et al., "Total-Transfer, Valve-Based Comprehensive Two-Dimensional Gas Chromatography", Analytica Chimica Acta, vol. 555, 2006, pp. 68-74.*

* cited by examiner

*Primary Examiner*—Daniel S Larkin

(57) ABSTRACT

The present invention is an improvement to two-dimensional comprehensive gas chromatography. The improvement is a two-valve switching modulator connecting two gas chromatography separation columns. The modulator is located between the first and second columns and includes two valves with transfer lines between the valves for switching a carrier gas between the transfer lines.

8 Claims, 6 Drawing Sheets

Valve position X

Valve position Y

TWO VALVE SWITCHING MODULATOR FOR COMPREHENSIVE TWO-DIMENSIONAL GAS CHROMATOGRAPHY

This application claims the benefit of U.S. Provisional Application 60/781,996 filed Mar. 14, 2006.

SUMMARY OF THE INVENTION

The present invention is an improvement to a comprehensive two-dimensional gas chromatography system. This improvement is a valve switching modulation system that has been designed and built for a comprehensive two-dimensional gas chromatography (GC×GC). This valve switching modulation system utilizes two four-port valve switches at the same time in each modulation period to achieve the modulation.

There are many advantages of the present invention. These include no need for any type of coolant. In addition, the first and the second-dimensional column flow are independently controlled.

Comprehensive two-dimensional gas chromatography (GC×GC) is a powerful separation technique that provides superior chromatographic type separation to a complex mixture. It is the most significant development in the gas chromatography technology area during recent years. The key to make a conventional GC into a comprehensive two-dimensional gas chromatography (GC×GC) is the modulation system. In the prior art, modulation is achieved by the trap and release mechanism called "thermal modulation". This method of modulation for GC×GC requires coolants (liquid nitrogen or liquid carbon dioxide) to operate. It is relatively inconvenient and it creates difficulty in the coolant handling situation, especially in the remote location or in the manufacture plant environment.

DETAILED DESCRIPTION OF THE PREFERRED EMBODIMENTS

Comprehensive two-dimensional gas chromatography (GC×GC) was introduced approximately ten years ago at the academic society. During the last ten years, scientists worldwide have demonstrated further that two-dimensional separation can be applied to complex mixtures. The major advantages of GC×GC technique are improved resolution (two-column separation) and enhanced sensitivity (modulation, in this case, is cyro-focusing). The flame-ionization detector (FID) results demonstrated advantage of superior separation that gives the class separation among paraffins and aromatics.

The GC×GC system includes an injector, then the two columns followed by a detector. A modulation system is located between the columns. The injector feeds the carrier or mobile phase into the first column. In the present invention, the carrier gas is branched prior to the injector.

The key to make a conventional GC into a comprehensive two-dimensional gas chromatography (GC×GC) is the modulation system. There are several ways to accomplish the modulation. One way is utilize the trap and release mechanism called thermal modulation. This type of modulation requires liquid nitrogen or liquid carbon dioxide as the coolant to accomplish the trapping process. The present invention shows another way. This way utilizes a differential flow mechanism called switching valve modulation. This type of modulation requires a differential flow and a switching valve(s) system to achieve the modulation. This invention is one type of differential flow modulation. The detailed design is shown in the FIG. 1.

Figure 1:
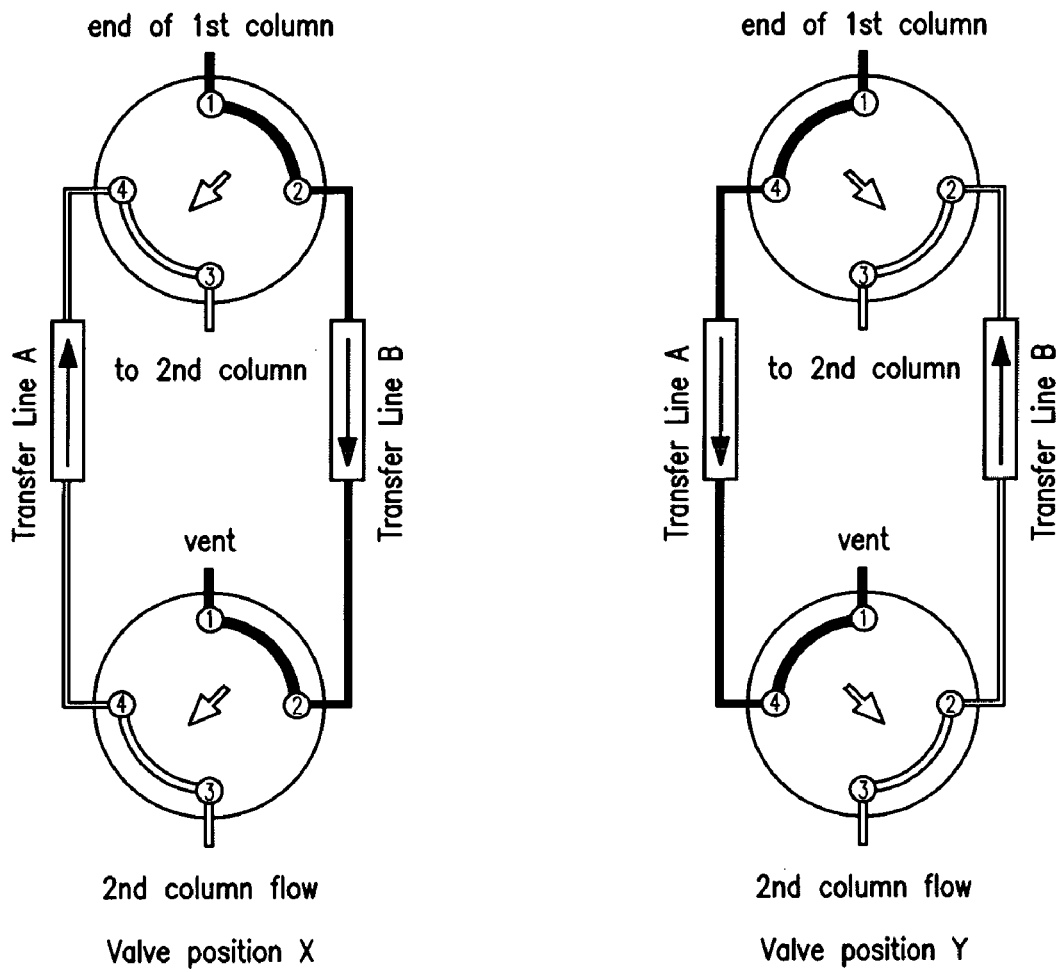
FIG. 1 shows a schematic diagram of the valve modulation system of the present invention.
Figure 2:
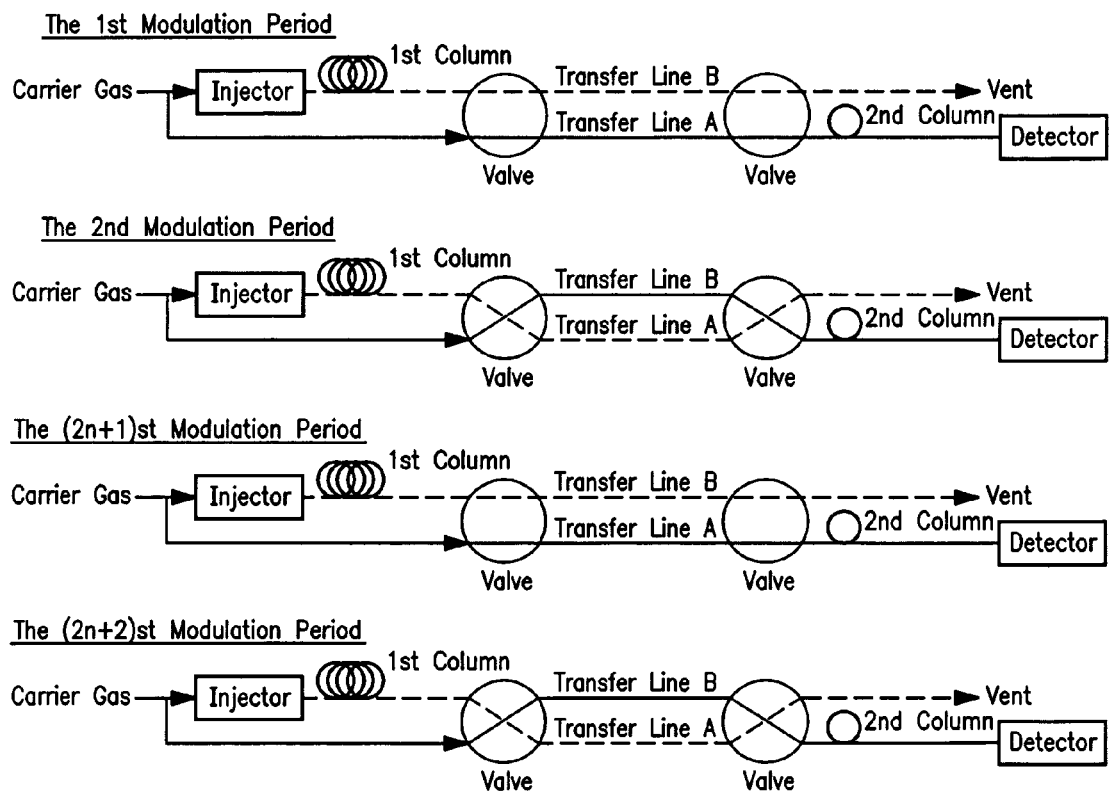
FIG. 2 shows a schematic diagram showing the flow of the fluid from the first column through the valve modulation system into the second column.

This modulation system accomplishes modulation by two valve switching at the same time in a modulation period. The system includes transfer lines A and B that transfer carrier gas and eluent as shown in FIGS. 1 and 2. Both transfer lines need to have exactly the same inner diameter and the same length. The detailed modulation process is explained below:

(1) When valves are in the position X in one modulation period (as left side valves in FIG. 1)
   (a) The eluent comes out from the first dimensional column and deposits to transfer line B; and
   (b) The second dimensional column flow sweeps the eluent deposited on transfer line A from the last modulation period to the second dimensional column.

(2) In the next modulation period, the valves are switched to position Y (as right side valves in FIG. 1)
   (a) The eluent come out from the first dimensional column and deposits to transfer line A; and
   (b) The second dimensional column flow sweeps the eluent deposited on transfer line B from the last modulation period to the second dimensional column.

This modulation system's continuous switching between the position X and Y through the entire experiment accomplishes the comprehensive two-dimensional gas chromatography.

FIG. 2 shows a diagram of the 2DGC-switching valves are system of the present invention showing the flow of fluid from the first column through the valve modulation system to the second column.

(1) In the first modulation period, both valves in the position X, the carrier gas flows through the injector, through the first dimensional column and moves eluent to transfer line B. The second column flow, which is a branch of carrier gas (branched before the injector) sweep through transfer line A and flow through the second dimensional column to the detector.

(2) In the second modulation period, both valves in the position Y, the carrier gas flow through injector, through the first dimensional column and moves eluent to transfer line A. The second column flow, which is a branch of carrier gas (branched before the injector) sweeps through transfer line B and flows through the second dimensional column to the detector.

(3) In the (2n+1)st modulation period, both valves are in the position X, the carrier gas flows through the injector, through the first dimensional column and moves eluent to transfer line B. The second column flow, which is a branch of carrier gas (branched before the injector) sweeps through transfer line A and flows through the second dimensional column to the detector.

(4) In the (2n+2)st modulation period, both valves are in the position Y, the carrier gas flows through the injector, through the first dimensional column and moves eluent to transfer line A. The second column flow, which is a branch of carrier gas (branched before the injector) sweeps through transfer line B and flows through the second dimensional column to the detector.

Figure 5:
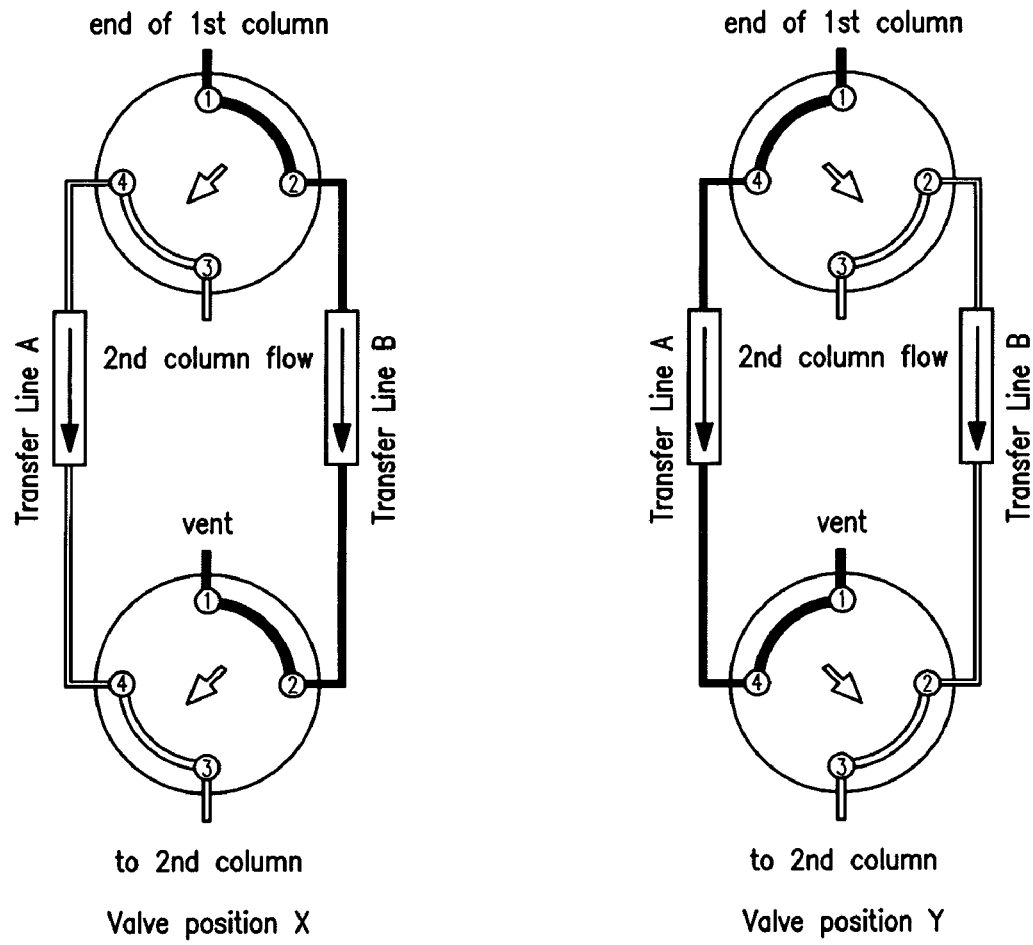
FIG. 5 shows a schematic diagram of an alternative arrangement of the comprehensive two-dimensional gas chromatography switching valve modulation system of the present invention.

Depending on the flow direction in the transfer line, the switching valve modulation system can also have different connections than what is illustrated in FIG. 1. FIG. 5 shows a schematic diagram of an alternative arrangement of the comprehensive two-dimensional gas chromatography switching valve modulation system of the present invention.

This modulation system accomplishes modulation by two valve switching at the same time in a modulation period. The detailed modulation process is explained exactly as that for the modulator valve system in FIG. 1.

(a) However, this modulation system reverses the switching between the valves in positions X and Y to accomplish the comprehensive two-dimensional gas chromatography. The difference between the FIG. 5 design and the FIG. 1 design is that in FIG. 1 the valve connects the end of the first column to the second column and in FIG. 5, the valve connects the end of first column to the second column flow. In the FIG. 1 design, the connection to the end of the first column and the connection to the second column are in the same valve. However, in the FIG. 5 design, the connection to the end of the first column and the connection to the second column are in the different valve.

The modulation system can also be built on two valves with more than four ports, however, because of extra loops and ports involved, it will not perform as simply and as well as four port valves.

Figure 6:
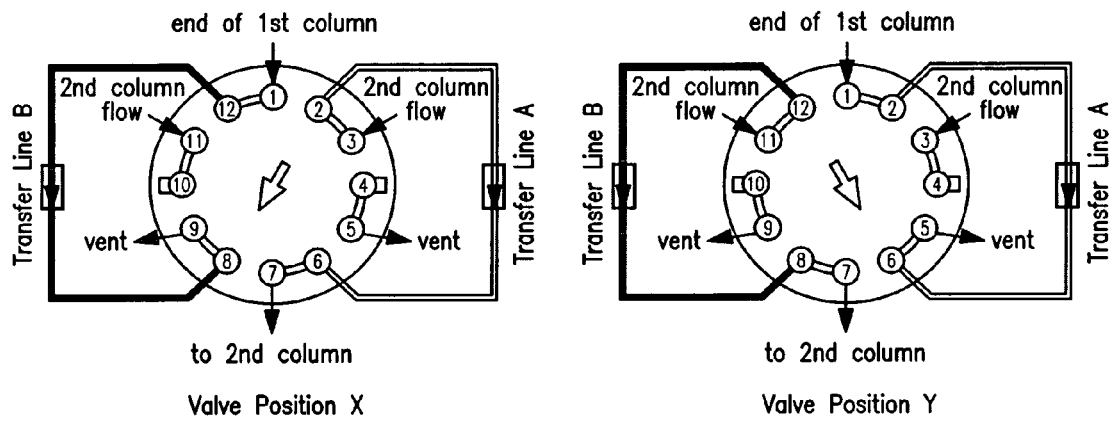
FIG. 6 shows a schematic diagram of valve modulation system including only one valve.

The modulation system can also be built on one valve with at least twelve ports. FIG. 6 shows a schematic diagram of valve modulation system including only one valve. The detailed modulation process is explained below:

(1) When valves are in the position X in the one modulation period (as left side valves in FIG. 6)
  (a) The eluent comes out from the first dimensional column flows through port 1 passing through port 12 and deposits to transfer line B and through port 8 and port 9 to vent; and
  (b) The second dimensional column flow passes the port 3 to port 2 and sweeps the eluent deposited on transfer line A from the last modulation period through port 6 to port 7 and to the second dimensional column.

(2) In the next modulation period, the valves are switched to position Y (as right side valves in FIG. 6)
  (a) The eluent comes out from the first dimensional column flows through port 1 passing through port 2 and deposits to transfer line A and through port 6 and port 5 to vent; and
  (b) The second dimensional column flows pass the port 11 to port 12 and sweeps the eluent deposited on transfer line A from the last modulation period through port 8 to port 7 and to the second dimensional column.

The modulation system can also be built on one valve with more than twelve ports, however, because of extra loops and ports involved, it will not perform as simply and as well as one twelve port valve.

Because the two valve switching modulation system makes the second dimensional column flow independent from the first dimensional column flows, the separation in the second dimensional column can be better controlled. By varying the flow in the second dimensional column, the separation among different components can be increased or decreased depending on the purpose or desire of the separation. Therefore, the peak width and the separation in the second dimensional column can be independently adjusted.

One of the other ways to control the separation in the second dimensional column is the temperature. Because the two valve switching modulation system makes the second dimensional column flow and the second dimensional column completely independent from the first dimensional column and the first dimensional column flow, the second dimensional column flow and the second dimensional column can be put into a separate oven to have a separated temperature to increase or decrease separation that will be depend on the purpose or desired of the separation.

EXAMPLES

Two examples are given to demonstrate the valve switching comprehensive two-dimensional gas chromatograph.

Example 1

The naphtha fuels used in this study are typical refinery streams boiling between 65° C. (150° F.) to 215° C. (420° F.) with a carbon number from approximately $C_5$ to $C_{12}$.

The Set-Up and Conditions

The GC×GC system consists of an Agilent 6890 gas chromatograph (Agilent Technology, Wilmington, Del.) configured with an injector, columns, and detectors. A split/splitness inlet system with an 100 tray autosampler is used. The two-dimensional capillary column system utilizes a weak-polar first column (007-1, 30 meter, 0.25 mm I.D., 5.0 μm film), (Quadrex Inc. Corp, Woodbridge, Conn., USA) and a polar (Sol-Gel Wax, 3 meter, 0.25 mm I.D., film), (SGE Inc. Austin, Tex.) second column. A switching two valve modulation assembly based on this invention is installed between these two columns. The valve is electrical actuated (VICI Valco Instruments Co. Inc., Houston, Tex., USA). The transfer line is a set of pre-cut 1/16 inch stainless steel tubing with 0.25 mmID and 20 cm length (Alltech Associate Inc. State College, Pa., USA). The detector is a Flame ionization detector (FID) which comes with the Agilent GC system.

A 1.0 μL sample was injected with a 50:1 split at 300° C. at a constant head pressure mode of 15 psi with an oven temperature of 36° C. The oven is programmed from 36° C. with a two minute hold and a 3° C. per minute increment to 240° C. with a zero minute hold and with a total run time of seventy minutes. The second column is at a constant head pressure of 8 psi. The modulation period is ten seconds. The sampling rate for the detector was 100 Hz.

Figure 3:
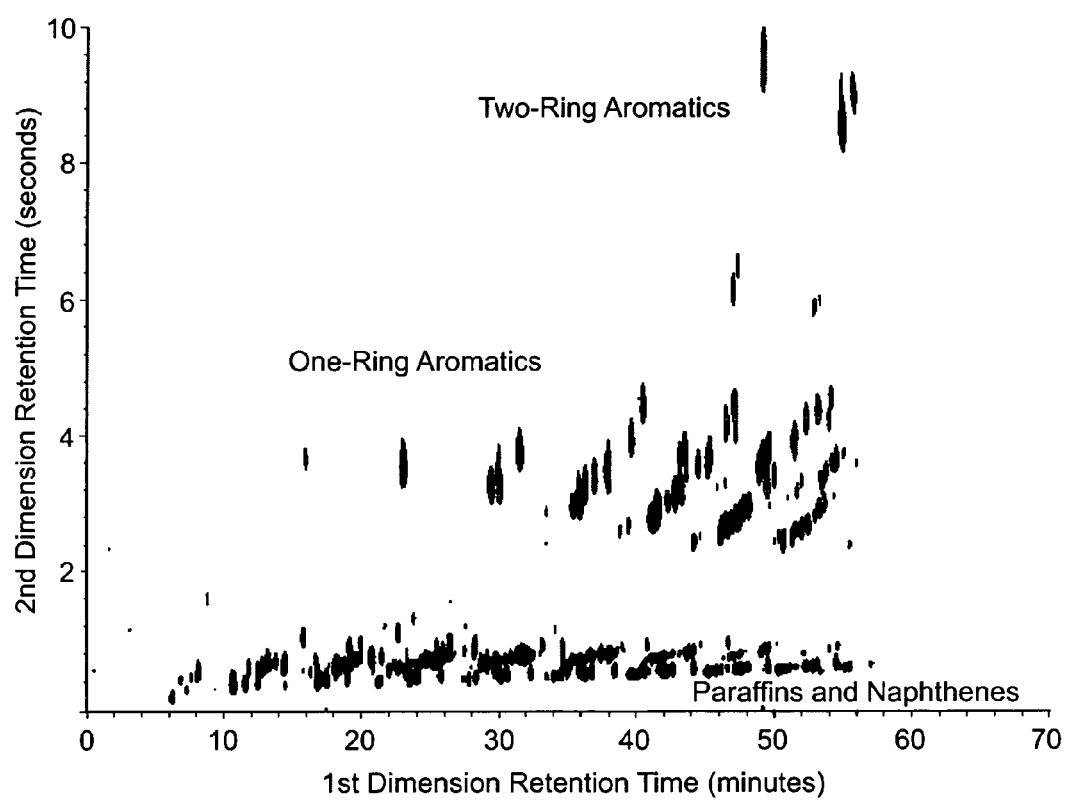
FIG. 3 shows a comprehensive two-dimensional gas chromatogram of naphtha using the valve modulation system of the present invention.

After data acquisition, it was processed for qualitative analysis. The qualitative analysis converts data to a two-dimensional image that is processed by a commercial program "Transform" (Research Systems Inc. Boulder, Colo.). The two-dimensional image is further treated by "Photo-Shop" program (Adobe System Inc. San Jose, Calif.) to generate publication-ready images. FIG. 3 is the comprehensive two-dimensional gas chromatogram of the naphtha.

FIG. 3 shows that the detailed composition of this naphtha can be displayed in this two-dimensional chromatogram. Every compound class is clearly separated in the second dimension. The two valve switching modulation has accomplished this low-temperature two-dimensional separation.

Example 2

The diesel fuels used in this study are typical refinery streams boiling between 150° C. (300° F.) to 430° C. (800° F.) with a carbon number from approximately $C_9$ to $C_{28}$.

The GC×GC system consists of an Agilent 6890 gas chromatograph (Agilent Technology, Wilmington, Del.) configured with an inlet, columns, and detectors. A split/splitness inlet system with an 100 tray autosampler is used. The two-dimensional capillary column system utilizes a weak-polar first column (SPB-1, 15 meter, 0.53 mm I.D., 1.0 µm film), (SUPELCO Inc. Bellefonte, Pa., USA) and a polar (Wax-10, 0.5 meter, 0.53 mm I.D., 1.0 µm film), (SUPELCO Inc. Bellefonte, Pa., USA) second column. A switching two valve modulation assembly based on this invention is installed between these two columns. The valve is electrical actuated (VICI Valco Instruments Co. Inc., Houston, Tex., USA). The transfer line is a set of pre-cut 1/16 inch stainless steel tubing with 0.50 mmID and 20 cm length (Alltech Associate Inc. State College, Pa., USA). The detector is a Flame ionization detector (FID) which comes with the Agilent GC system.

A 1.0 µL sample was injected with a 20:1 split at 300° C. at a constant head pressure mode of 3 psi with an oven temperature of 60° C. The oven is programmed from 60° C. with 2° C. per minute increments to 240° C. with a zero minute hold and with a total run time of ninety minutes. The second column is programmed with a head pressure from 2.0 psi and 0.01 psi increment to 2.9 psi. The modulation period is 10 seconds. The sampling rate for the detector was 100 Hz.

Figure 4:
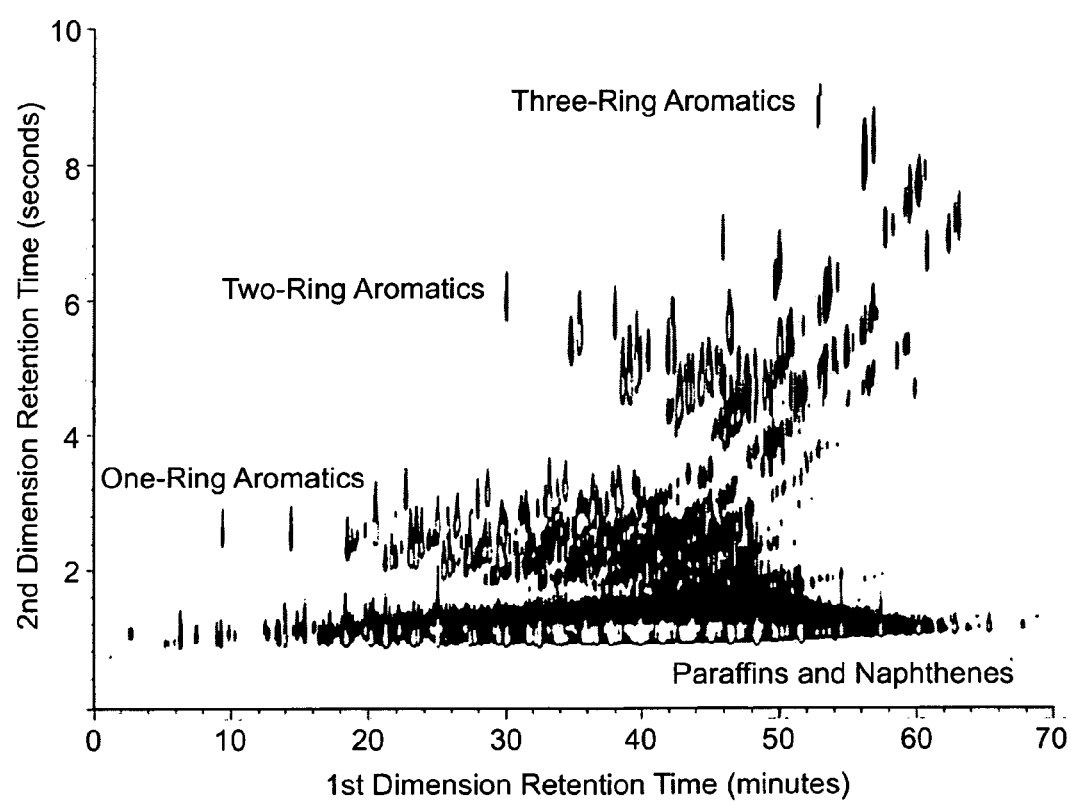
FIG. 4 shows a comprehensive two-dimensional gas chromatogram of diesel using the valve modulation system of the present invention.

After data acquisition, it was processed for qualitative analysis. The qualitative analysis converts data to a two-dimensional image that is processed by a commercial program "Transform" (Research Systems Inc. Boulder, Colo.). The two-dimensional image is further treated by "PhotoShop" program (Adobe System Inc. San Jose, Calif.) to generate publication-ready images. FIG. 4 is the comprehensive two-dimensional gas chromatogram of the diesel.

FIG. 4 shows the detailed composition of this diesel can be displayed in this two-dimensional chromatogram. Every compound class is clearly separated in the second dimension. The two valve switching modulation has accomplished this high temperature two-dimensional separation.

What is claimed is:

1. A modulator for a two-dimensional comprehensive Gas Chromatography system (GC×GC) including a first dimensional column and a second dimensional column wherein said modulator is located between the first and second columns and wherein said modulator comprises a two valves with transfer lines between said valves for switching a carrier gas between the transfer lines.

2. The modulator of claim 1 wherein the two valve switching modulator maintains a carrier gas through both chromatographs.

3. The modulator of claim 2 wherein
said carrier gas is helium, or hydrogen or nitrogen or other inert (non-reactive gas).

4. The modulator of claim 3 wherein said modulator includes two valves and two transfer lines.

5. The modulator of claim 4 wherein said transfer lines have the same length and same inner diameter.

6. The modulator of claim 5 wherein said modulator that connects the first dimensional column, the second dimensional column, the second dimensional column flow, and the vent can have more than one type of valve.

7. The modulator of claim 6 wherein said the second dimensional column flow can be independently controlled.

8. The modulator of claim 7 wherein said the second dimensional column temperature can be independently controlled.

* * * * *